United States Patent [19]
Bobee et al.

[11] Patent Number: 5,460,829
[45] Date of Patent: Oct. 24, 1995

[54] PHARMACEUTICAL COMPOSITIONS BASED ON EBASTINE OR ANALOGUES THEREOF

[75] Inventors: Jean-Marc Bobee, Verriéres-le-Buisson; Guillaume Conrath, Châtenay-Malabry; Gabriel Gousset, Le-Plessis-Robinson; Michel Ponsot, Fonenay-aux-Roses; Michel Veillard, Sceaux, all of France

[73] Assignee: Rhone-Poulenc Rorer S.A., Antony, France

[21] Appl. No.: 244,204

[22] PCT Filed: Dec. 1, 1992

[86] PCT No.: PCT/FR92/01116

§ 371 Date: Jun. 1, 1994

§ 102(e) Date: Jun. 1, 1994

[87] PCT Pub. No.: WO93/10782

PCT Pub. Date: Jun. 10, 1993

[30] Foreign Application Priority Data

Dec. 3, 1991 [FR] France ................... 91 14936

[51] Int. Cl.$^6$ ................................. A61K 31/445
[52] U.S. Cl. .................. 424/489; 514/326; 514/327; 424/1.29
[58] Field of Search .................. 514/326, 327; 424/489

[56] References Cited

U.S. PATENT DOCUMENTS

| | | | |
|---|---|---|---|
| 4,550,116 | 10/1985 | Soto et al. | 514/327 |
| 4,829,064 | 5/1989 | Sunshine et al. | 514/255 |
| 4,871,733 | 10/1989 | Sunshine et al. | 514/212 |
| 4,975,426 | 4/1990 | Sunshine et al. | 514/159 |
| 5,021,242 | 6/1991 | Römer et al. | 424/489 X |
| 5,202,129 | 4/1993 | Samejima et al. | 424/489 |
| 5,271,944 | 12/1993 | Lee | 424/489 |
| 5,356,887 | 10/1994 | Brenner et al. | 514/108 |

FOREIGN PATENT DOCUMENTS

| | | |
|---|---|---|
| 0134124 | 3/1985 | European Pat. Off. . |
| 88/08302 | 11/1988 | WIPO . |
| 88/09656 | 12/1988 | WIPO . |
| 89/10143 | 11/1989 | WIPO . |

*Primary Examiner*—Richard L. Raymond
*Attorney, Agent, or Firm*—Finnegan, Henderson, Farabow, Garrett & Dunner

[57] ABSTRACT

This invention relates to the process for the preparation of novel 1,4-substituted piperidine derivative based solid compositions in micronized or hydrophilic form.

9 Claims, No Drawings

PHARMACEUTICAL COMPOSITIONS BASED ON EBASTINE OR ANALOGUES THEREOF

FIELD OF THE INVENTION

The present invention relates to a novel pharmaceutical form based on 1,4-substituted piperidine derivatives.

DESCRIPTION OF THE INVENTION

The pharmaceutical compounds which are the subject of the formulation described in the present invention are described in European Patent Application EP 134,124, which is included in the present Application by incorporation by reference.

These compounds, and even more specifically the following compound, for which the internationally recognized name is ebastime or 4-diphenylmethoxy-1-[3-(4-tert-butylbenzoyl)propyl]piperidine of formula:

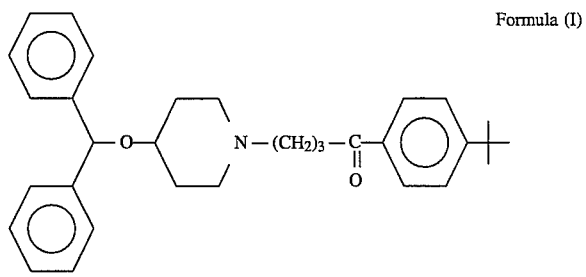

Formula (I)

display, when they are formulated in solid form, a very mediocre bioavailability. This insufficient bioavailability is in part linked to a poor water solubility. It is thus difficult, from the crude starting material described in the abovementioned patent, to place it in a solid form which may be used by man, and which displays a correct bioavailability and, consequently, a correct biological activity. The compound of formula (I), in the form of a salt, and more particularly in the form of the lactate, has an optimum solubility, at pH 2, which is equal to 0.8 mg/ml; the compound of formula (I) in basic non-salified form has an even lower water solubility.

These compounds have an antihistamine $H_1$ activity and are useful for treating respiratory, allergic or cardiovascular diseases. Thus, they relax vascular and bronchial smooth muscles in vitro and in vivo.

They also inhibit the constricting effect of adrenaline and of potassium ions, both in the intestine and in the trachea. Thus, they block the bronchoconstriction induced by histamine aerosols at doses as low as 1 mg/kg.

These compounds are active via the parenteral route as well as the oral route. During their oral administration, the active principle of formula (I), due to its low solubility in water, requires a very long dissolution time in the aqueous medium of the stomach, which may result in a loss of the active principle, which remains undissolved and is thus not absorbable, during emptying of the gastric system, and may thus result in the use of an overdose, which is always dangerous in the medical field. Thus, in the abovementioned patent application, that is to say European Patent Application EP 134,124, when tablets are prepared, according to Example 9 which is the only example to describe a tablet form, dissolution of the active principle in an acidic medium is extremely slow.

The present invention has sought to develop a new solid administration form for the compounds of formula (II) below, in which the active principle displays an improved solubility and thus an improved bioavailability.

The present invention relates to a new solid form based on compounds corresponding to the following formula (II):

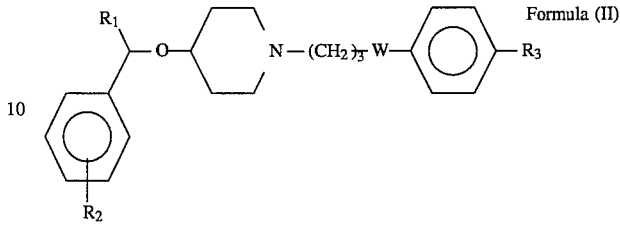

Formula (II)

in which:

$R_1$ represents a thienyl group, a phenyl group optionally substituted with a halogen, an alkoxy group containing 1 to 6 carbon atoms or an alkyl group containing i to 6 carbon atoms, $R_2$ represents a halogen atom, a hydrogen atom, an alkoxy group containing 1 to 6 carbon atoms or an alkyl group containing 1 to 6 carbon atoms, $R_3$ represents a halogen atom, a hydrogen atom, an alkoxy group containing 1 to 6 carbon atoms, an alkyl group containing 1 to 6 carbon atoms, an alkylthio group containing 1 to 6 carbon atoms, a cycloalkyl group containing 5 or 6 carbon atoms or a group of formula:

where R4 and R5 represent, independently of each other, a hydrogen atom or an alkyl group containing 1 to 6 carbon atoms, R6 represents a cycloalkyl group containing 3 to 6 carbon atoms or a hydroxymethyl or carboxyl group or an alkoxycarbonyl group containing 2 to 7 carbon atoms, W represents a carbonyl or hydroxymethylene group, and their salts; characterized in that the active principle of formula (II) is micronized.

This form has the advantage of displaying an initial rate of dissolution which is approximately 40% higher than the pharmaceutical form obtained from a non-micronized compound of formula (II).

According to a form which is further improved in terms of dissolution of the compounds of formula (II), in addition to the micronization, a hydrophilization of the product is carried out, which enables it to achieve a dissolution rate which is approximately 300% improved relative to the solid form containing a compound of formula (II) which has undergone neither a step of micronization nor a step of hydrophilization.

According to one example of the implementation of the invention, the crude crystallized compound of formula (I) is introduced into a micronizer fitted with a filtering sleeve and a supply hopper. Cooled compressed air is injected in order to fractionate the particles. The micronized product obtained which is preferred displays the following characteristics:

maximum size smaller than 200 μm number average particle size between 0.5 and 15 μm preferably with 90%, by number, of particles having a particle size smaller than 25 μm, and preferably smaller than 20 μm.

The micronized powder may subsequently be given the final pharmaceutical form, for example in compressed form by direct compression or moist granulation, or alternatively in the form of oral lyophilizates or gelatin capsules.

According to a second, better way of implementing the invention, the micronized powder obtained is hydrophilized. The hydrophilization is performed by spraying with water. The amount of water introduced is preferably between 10 and 30 g of water per 100 g of micronized powder. This hydrophilization may be performed at the same time as the granulation, in which case a moist granulation is carried out.

For the compressed formulation it is possible either to perform a direct compression on the micronized and non-hydrophilized powder or to perform a compression on the hydrophilized and granulated powder.

For the formulation of oral lyophilizates the active principle of formula (II) is mixed with:

- a sweetener chosen, for example, from aspartame or sodium saccharinate
- a binding agent, in particular such as dextran
- a diluent such as, for example, mannitol or lactose.

The present invention will be more fully described with the aid of the examples which follow, which should not be considered as limiting the invention.

MICRONIZATION

This is performed in a stainless steel micronizer of diameter 200 mm having a filtering sleeve made from polyester. The supply hopper is also made from stainless steel. The compressed air used is dehydrated by refrigeration.

The injection of compressed air brings about the acceleration of the particles in the micronizer plate; the particles which collide with each other become fractionated into increasingly finer particles.

| CRUDE PRODUCT | MICRONIZED PRODUCT |
|---|---|
| 97.7% < 500 μm | 100% < 80 μm |
| 94.4% < 400 μm | 99.4% < 50 μm |
| 76% < 225 μm | 97.6% < 25 μm |
| 43.4% < 125 μm | 96.6% < 20 μm |
| 23.7% < 83 μm | 93.1% < 15 μm |
| 8.1% < 46 μm | 90.3% < 10 μm |
| 2.5% < 20 μm | 61.1% < 5 μm |
| Average size = 140 μm | 31.1% < 2 μm |
|  | 18% < 1 μm |
|  | Average size = 3.4 μm |

PREPARATION OF THE TABLETS

The following products are used for the preparation of this composition:

| | |
|---|---|
| Ebastime (compound of formula (I)) | 10.0 mg |
| Microcrystalline cellulose | 20.0 mg |
| Lactose monohydrate | 88.5 mg |
| Pre-gelified starch | 5.2 mg |
| Crosslinked sodium carboxymethyl cellulose | 5.0 mg |
| Magnesium stearate | 1.3 mg |
| For a tablet of | 130.0 mg |

EXAMPLE 1 AND COMPARATIVE EXAMPLE 1

1—DIRECT COMPRESSION—Experimental procedure (test size 520 g)

1°—Sieve on a sieve of mesh size 0.630 mm the following products:

Micronized or non-micronized ebastime (Examples 1 and C1)

Microcrystalline cellulose of average particle size equal to 200 μm

Lactose monohydrate of average particle size equal to 200 μm

Pre-gelified starch

2°—Mix for 15 minutes in a Turbula type apparatus

3°—Sieve the magnesium stearate and the crosslinked sodium carboxymethyl cellulose on a sieve of mesh size 0.5 mm 4°—Mix for 5 minutes in a Turbula type apparatus.

EXAMPLE 2 AND COMPARATIVE EXAMPLE 2

2—MOIST GRANULATION—Experimental procedure (test size 520 g)

1°—Place in the tank of a small planetary mixer (Kenwood type):

Microcrystalline cellulose

Lactose monohydrate

Pre-gelified starch

Micronized or non-micronized ebastime (Examples 2 and C2)

2°—Mix for 10 minutes

3°—Moisten with 23% of purified water (calculation made relative to the total mass used)

4°—Granulate for 10 minutes

5°—Dry in a ventilated oven for 6.5 hours at 50° C.

6°—Even out the grain obtained by passing through a sieve of mesh size 0.8 mm

7°—Sieve the magnesium stearate and the crosslinked sodium carboxymethyl cellulose on a sieve of mesh size 0.5 mm and add these two excipients to the grain previously obtained 8°—Mix using a Turbula type apparatus for 10 minutes.

3—COMPRESSION

In both cases, compress on a FROGERAIS OA alternating machine equipped with punches of diameter 7 mm and having a radius of curvature of 8 mm.

The target average weight for these tablets is 130 mg. The machine is also adjusted so that these tablets have a breaking strength of 50 newtons (Sleuninger apparatus).

The percentage of compound of formula (I) dissolved, after 45 minutes, in 0.1N hydrochloric acid medium is measured. The dissolution test is performed in the apparatus with blades described in the European Pharmacopoeia 2nd Edition V 5.4 (1986) and in USP XXII <711>. The test sample is 6 tablets. The dissolution medium contains 1000 ml of 0.1N hydrochloric acid and the rotational speed of the blade is 100 revolutions/minute. The assay is carried out by ultraviolet spectrophotometry at a wavelength of 258 nanometers in 1 cm cells (E 1% 1 cm=366). The results are outlined in Table (I)

TABLE (I)

| TESTS | COMPOUND OF FORMULA (I) | PRODUCTION OF THE TABLET | DEGREE OF DIS-SOLUTION |
|---|---|---|---|
| C1 | Non-micronized | Direct compression | 26.4% |
| C2 | Non-micronized | Moist granulation | 36.7% |
| 1 | Micronized | Direct compression | 52.6% |
| 2 | Micronized | Moist granulation | 94.0% |

EXAMPLE 3—PREPARATION OF ORAL LYOPHILIZATES

The following composition is used:

| | |
|---|---|
| Ebastime (micronized) | 5.00 mg |
| Xanthan gum | 0.12 mg |
| Aspartame | 5.00 mg |
| Docusate sodium | 0.25 mg |
| Dextran 70 | 20.00 mg |
| Mannitol | 669.63 mg |
| Water | 525.00 mg |

The docusate sodium is dissolved in 90% of the water, with stirring in a turbine for 30 minutes at room temperature. The xanthan gum is added and stirring is carried out for 30 minutes until dissolution is complete. The dextran is dispersed in this solution until a clear solution is obtained.

The micronized ebastine, aspartame and mannitol are introduced into a planetary mixer, mixing is carried out at reduced pressure (0.2 bar) for 30 minutes and the solution is then introduced into the mixture of powders, the solution container is rinsed with the remainder of the water and the rinsings are introduced into the mixer. The paste is kept stirring for 30 minutes. The paste is divided into 1.6 ml PVC cells.

Freeze-drying is performed in a freeze-dryer.

Oral lyophilizates are obtained, with an average mass of 700 mg, having an average ebastine assay of 4.90 mg per lyophilizate and containing 0.26% of water.

The lyophilizates taste fresh and sweet without bitterness.

The spoon disintegration test is performed and gives an average time of 45 s.

This time corresponds to the period required in order to obtain complete disintegration of an oral lyophilizate subjected to a constant stirring (spoon rotating at 200 revolutions/minute) in a 400 ml beaker containing 200 ml of distilled water (water temperature=20° C.). Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. Solid pharmaceutical composition having improved dissolution properties, comprising a compound of the formula:

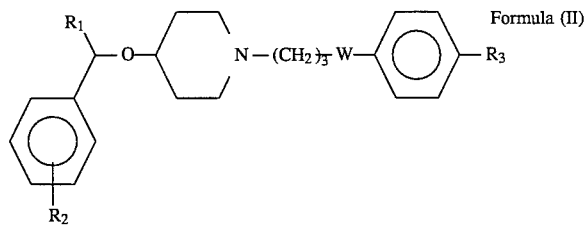

Formula (II)

in which:

$R_1$ represents a thienyl group, a phenyl group optionally substituted with a halogen, an alkoxy group containing 1 to 6 carbon atoms or an alkyl group containing 1 to 6 carbon atoms, $R_2$ represents a halogen atom, a hydrogen atom, an alkoxy group containing 1 to 6 carbon atoms or an alkyl group containing to 6 carbon atoms, $R_3$ represents a halogen atom, a hydrogen atom, an alkoxy group containing 1 to 6 carbon atoms, an alkyl group containing 1 to 6 carbon atoms, an alkylthio group containing 1 to 6 carbon atoms, a cycloalkyl group containing 5 or 6 carbon atoms or a group of formula:

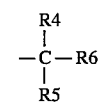

where R4 and R5 represent, independently of each other, a hydrogen atom or an alkyl group containing 1 to 6 carbon atoms, R6 represents a cycloalkyl group containing 3 to 6 carbon atoms or a hydroxymethyl or carboxyl group or an alkoxycarbonyl group containing 2 to 7 carbon atoms, W represents a carbonyl or hydroxymethylene group, and their salts; wherein the compound of formula (II) is micronized, such that said compound of formula (II) has the following characteristics:
maximum size smaller than 200 μm,
number average particle size between 0.5 and 15 μm.

2. Composition according to claim 1, wherein $R_1$ represents a phenyl group $R_2$ represents hydrogen $R_3$ represents a tert-butyl group W represents a carbonyl group.

3. Composition according to claim 1, wherein the compound of formula (II) is hydrophilized.

4. Composition in compressed form comprising the compound of claim 1.

5. Process for the preparation of compositions according to claim 4, comprising:

performing a micronization of the compound of formula (II) in a first step, performing a direct compression in a second step.

6. Process for the preparation of compositions according to claim 4, comprising:

performing a micronization of the compound of formula (II) in a first step, performing a moist granulation, followed by a compression, in a second step.

7. Compositions in the form of oral lyophilizates, comprising the compound of formula II according to claim 1, a suspension agent selected from gums, a sweetener and a diluent.

8. Compositions according to claim 1, wherein 90% by number, of particles have a particle size smaller than 25 μm.

9. Compositions according to claim 8, wherein the particle size is smaller than 20 μm.

* * * * *

UNITED STATES PATENT AND TRADEMARK OFFICE
CERTIFICATE OF CORRECTION

PATENT NO. : 5,460,829
DATED : October 24, 1995
INVENTOR(S) : Bobee, Conrath, Gousset, Ponsot & Veillard It is certified that error appears in the above-indentified patent and that said Letters Patent is hereby corrected as shown below:

Claim 1, col. 6, line 6, "to 6" should read --1 to 6--.

Signed and Sealed this

Twenty-third Day of January, 1996

Attest:

BRUCE LEHMAN

*Attesting Officer*          *Commissioner of Patents and Trademarks*